United States Patent [19]

Barth

[11] 4,026,881

[45] May 31, 1977

[54] 6-(D-2-[4-HYDROXY-1,5-NAPHTHYRIDINE-3-CARBOXAMIDO]-2-[4-HYDROXY-PHENYL]ACETAMIDO)-2,2-DIMETHYL-3-(5-TETRAZOLYL)PENAM

[75] Inventor: Wayne E. Barth, East Lyme, Conn.

[73] Assignee: Pfizer Inc., New York, N.Y.

[22] Filed: Apr. 16, 1976

[21] Appl. No.: 677,725

[52] U.S. Cl. .................. 260/239.1; 260/306.7 C; 424/271

[51] Int. Cl.² ............. C07D 499/28; C07D 499/00; C07D 499/70

[58] Field of Search ............... 260/239.1, 306.7 C

[56] References Cited

UNITED STATES PATENTS 3,954,733   5/1976   Tobiki et al. ................... 260/239.1

FOREIGN PATENTS OR APPLICATIONS 12,574   1/1975   Iran ............................... 260/239.1

*Primary Examiner*—Gerald A. Schwartz
*Attorney, Agent, or Firm*—Connolly and Hutz

[57]   ABSTRACT

6-(D-2-[4-Hydroxy-1,5-naphthyridine-3-carboxamido]-2-[4-hydroxyphenyl]acetamido)-2,2-dimethyl-3-(5-tetrazolyl)penam and the salts thereof are valuable antibacterial agents, particularly for the control of bacterial infections in mammals, especially man.

4 Claims, No Drawings

6-(D-2-[4-HYDROXY-1,5-NAPHTHYRIDINE-3-CARBOXAMIDO]-2-[4-HYDROXYPHENYL]ACETAMIDO)-2,2-DIMETHYL-3-(5-TETRAZOLYL)PENAM

BACKGROUND OF THE INVENTION

Belgian Pat. No. 821,163, granted Apr. 17, 1975 on an application filed on my behalf, and also my pending U.S. patent application Ser. No. 561,147 filed Mar. 24, 1975, disclose a broad genus of antibacterial agents of the formula I, wherein $R^1$ is an acyl group of an organic carboxylic acid. Additionally, the same broad genus of compounds is the subject matter of Iranian Pat. No. 12574, issued Jan. 12, 1975; African and Malagasy Republic Pat. No. 04798, issued Dec. 12, 1974; Lebanese Pat. No. 4088, issued Dec. 5, 1974; Paraguayan Pat. No. 2512, issued Apr. 8, 1975; Vietnamese Pat. No. 2647, issued Jan. 29, 1975 and now abandoned; and Zaire Pat. No. 1697/74, issued Mar. 12, 1975. However, it has now been discovered that the compound of the formula I, wherein $R^1$ is a 2-[4-hydroxy-1,5-naphthyridine-3-carboxamido]-2-[4-hydroxyphenyl]acetyl group, which is not specifically disclosed in said Belgian Pat. No. 821,163 or said pending United States patent application Ser. No. 561,147 L shows especially valuable antibacterial properties. In particular, the compound of the formula I, wherein $R^1$ is 2-[4-hydroxy-1,5-naphthyridine-3-carboxamido]-2-[4-hydroxyphenyl]acetyl possesses important advantages over the structurally most-closely related analogues disclosed in the said Belgian patent and the said United States patent application.

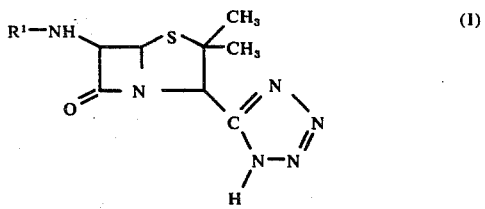

(I)

SUMMARY OF THE INVENTION

The present invention relates to 6-(D-2-[4-hydroxy-1,5-naphthyridine-3-carboxamido]-2-[4-hydroxyphenyl]acetamido)-2,2-dimethyl-3-(5-tetrazolyl)penam, the compound of the formula II, and the salts thereof, said compound of formula II and the salts thereof being of value as broad-spectrum antibacterial agents.

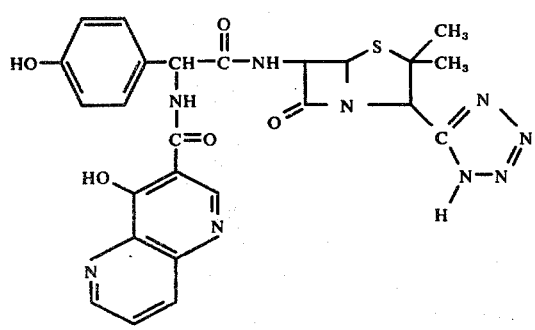

(II)

DETAILED DESCRIPTION OF THE INVENTION

This invention relates to the compound of the formula II. The compound II can be named as a derivative of "penam," which has been defined by Sheehan et al. in the *Journal of the American Chemical Society*, 75, 3293(1953), as referring to the structure:

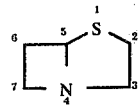

Although the term penam does not normally carry any stereochemical implications, the absolute stereochemistries (absolute configurations) of the compound of this invention at positions 3, 5 and 6 correspond to those found in the penicillins normally obtained by fermentation. Additionally, in the compound of this invention, the asymmetrically substitute carbon atom in the 2-[4-hydroxy-1,5-naphthyridine-3-carboxamido]-2-(4-hydroxyphenyl]acetyl group attached to C-6 of the penam nucleus is in the (R)-configuration. By analogy with nomenclature used in peptide chemistry, and in line with common practice in naming penam compounds, this is also designated as the D-configuration.

The compound of the present invention is a 5-substituted tetrazole compound, and such compounds can exist in two forms, viz:

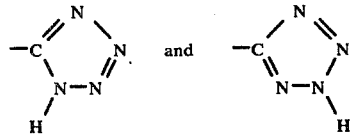

As will be appreciated by on skilled in the art, in a given compound these two forms co-exist in a dynamic, tautomeric, equilibrium mixture. For the sake of simplicity in this specification, the compound of the invention will be shown only in the form wherein the hydrogen atom is at the 1 position of the tetrazole ring; however, it is to be understood that this invention embraces the compound wherein the nitrogen atom is at the 1-position of the tetrazole ring, the compound wherein the hydrogen atom is at the 2-position of the tetrazole ring, an mixtures thereof.

It should also be noted that the 4-hydroxy-1,5-naphthyridine grouping in the compound of the present invention is a tautomeric system, which can be depicted, and named, as a 1,4-dihydro-4-oxo-1,5-naphthyridine group.

In one method according to the invention, the compound of the formula II is prepared by acylation of 6-(D-2-amino-2-[4-hydroxyphenyl]acetamido)-2,2-dimethyl-3-(5-tetrazolyl)penam, the compound of the formula III, with an activated derivative of 4-hydroxy-1,5-naphthyridine-3-carboxylic acid, the compound of the formula IV.

(III)

-continued

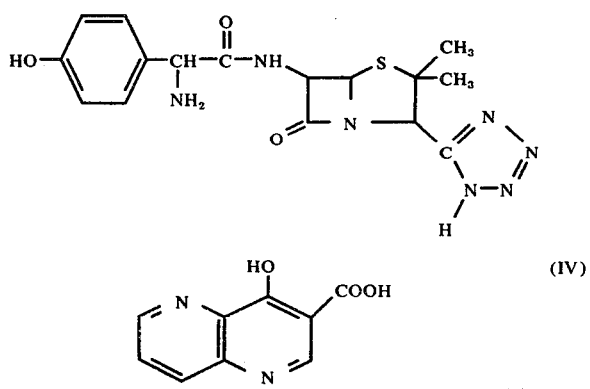

In a typical procedure, the 4-hydroxy-1,5-naphthyridine-3-carboxylic acid is activated via treatment of its triethylamine salt with ethyl chloroformate in hexamethylphosphoramide, and then the mixed anhydride thus formed is used in situ to acylate the compound of the formula III, also in hexamethylphosphoramide. The reaction mixture is then added to an excess of water at pH 2.5, and this causes the product to precipitate. It is recovered by filtration and can be purified further by standard procedures if desired.

6-(D-2-Amino-2-[4-hydroxyphenyl]acetamido)-2,2-dimethyl-3-(5-tetrazolyl)penam is prepared by the method disclosed in Belgian Pat. No. 821,163. The 4-hydroxy-1,5-naphthyridine-3-carboxylic acid is prepared from 3-aminopyridine by condensation with diethyl 2-(ethoxymethylene)malonate, followed by thermal cyclization to ethyl 4-hydroxy-1,5-naphthyridine-3-carboxylate, followed by alkaline hydrolysis. See Adams et al., *Journal of the American Chemical Society*, 68, 1317 (1946).

By virtue of the acidic nature of 5-monosubstituted tetrazole compounds, the 6-(D-2-[4-hydroxy-1,5-naphthyridine-3-carboxamido]-2-[4-hydroxyphenyl]-2,2-dimethyl-3-(5-tetrazolyl)penam compound of this invention forms salts with basic agents, and all such salts are to be considered within the scope of this invention. Salts which are of particular value are alkali metal salts, alkaline earth metal salts, as well as salts formed from organic amines. Especially valuable salts are the sodium and potassium salts.

The salts of the compound of the formula II are prepared by standard techniques, such as contacting the acidic and basic components, usually in a 1:1 molar ratio, in an aqueous, non-aqueous or partially aqueous medium, as appropriate. They are then recovered by filtration, by precipitation followed by filtration, by evaporation of the solvent, or, in the case of aqueous solutions, by lyophilization, as appropriate. Basic agents which are suitably employed in salt formation include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine, p-toluidine and octyl-amine; secondary amines, such as diethylamine, N-methylaniline, morpholine, pyrrolidine and piperidine; tertiary amines, such as triethylamine, N,N-dimethylaniline, N-ethylpiperidine, N-methylmorpholine and 1,5-diazabicyclo[4.3.0]non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; and bicarbonates, such as sodium bicarbonate and potassium bicarbonate.

The compound of the formula II and the salts thereof show outstanding and unexpected antibacterial activity in vitro against a wide variety of gram-positive and gram-negative organisms. This in vitro activity can be demonstrated using the conventional two-fold serial dilution technique. In practice, agar plates having the test compound incorporated therein at the various concentrations are inoculated with a standard number of the appropriate organism. The plates are incubated for 18 hours at 37° C., and then each plate is observed visually for the presence of growth of bacteria. The minimum inhibitory concentration (MIC), which is the lowest concentration of test compound which prevents growth of the microorganisms in question, is then noted. Microorganisms against which the compound of the formula II and its salts show activity are, for example, strains of *Staphylococcus aureus, Streptococcus pyogenes, Escherichia coli, Klebsiella pneumoniae, Proteus mirabilis* and *Pseudomonas aeruginosa*.

The in vitro antibacterial activity of the compound of the formula II and the salts thereof makes them valuable as industrial antimicrobials, for example in water treatment, slime control, paint preservation and wood preservation, as well as for topical application as disinfectants. In the case of use of these compounds for topical application it is often convenient to admix the active ingredient with a non-toxic carrier, such as vegetable or mineral oil or an emollient cream. Similarly, it can be dissolved or dispersed in liquid diluents or solvents such as water, alkanols, glycols or mixtures thereof. In most instances it is appropriate to employ concentrations of active ingredients of from about 0.1 percent to about 10 percent by weight, based on total composition.

Additionally, the compound of the formula II, and the pharmaceutically-acceptable (i.e. non-toxic) salts thereof, show outstanding and unexpected antibacterial activity in vivo. In determining such activity, the test compound is administered to mice which have been infected by intraperitoneal injection of a lethal inoculum of pathogenic bacteria. The test compound is administered using a multiple dosing regimen, using the subcutaneous (SC) route. The inoculum of bacteria varies from one to about ten times the amount needed to kill 100% of the mice, under the conditions of the test. At the end of the test, the activity of a compound is assessed by counting the number of survivors among the treated animals, and expressing the activity of a compound as the percentage of animals which survive. The compond of the formula II and its pharmaceutically-acceptable salts show valuable in vivo antibacterial activity against, for example, strains of *Staphylococcus aureus, Escherichia coli, Klebsiella pneumoniae* and *Pseudomonas aeruginosa*.

The in vivo antibacterial activity of the compound of the formula II and the pharmaceutically-acceptable salts thereof makes them suitable for the control of bacterial infections in mammals, including man, particularly by the parenteral route of administration. The compound of the formula II and the pharmaceutically-acceptable salts thereof will find wide use in the control of infections caused by susceptible gram-positive and gram-negative bacteria in human subjects.

When considering therapeutic use of the compound of the formula II, or a salt thereof, in a mammal, particularly man, the compound can be administered alone, or it can be mixed with other antibiotic substances and/or pharmaceutically-acceptable carriers or diluents, in accordance with standard pharmaceutical practice. Thus, for parenteral administration, which includes intramuscular, intraperitoneal, subcutaneous and intravenous use, sterile solutions of the active ingredient are usually prepared, and the pH of the solutions are suitably adjusted and buffered. For intravenous use, the total concentration of solutes should be controlled to render the preparation isotonic.

When a compound of the present invention is used in man, the daily dosage to be used will not differ significantly from other, clinically-used, penam antibiotics. The prescribing physican will ultimately determine the appropriate dose for a given human subject, and this can be expected to vary according to the age, weight, and response of the individual patient, as well as the nature and the severity of the patient's symptoms. However, the compounds of this invention will normally be used parenterally at dosages from about 10 to about 400 mg. per kilogram of body weight per day. These figures are illustrative only, however, and in some cases it may be necessary to use dosages outside these limits.

The following examples and preparation are provided solely for the purpose of further illustration.

EXAMPLE I 6-(D-2-[4-Hydroxy-1,5-naphthyridine-3-carboxamido]-2-[4-hydroxyphenyl]acetamido)-2,2-dimethyl-3-(5-tetrazolyl)penam To a solution of 4.20 ml (0.030 mol) of triethylamine in 50 ml. of hexamethylphosphoramide is added 2.85 g. (0.015 mol) of 4-hydroxy-1,5-naphthyridine-3-carboxylic acid. The mixture is stirred for 15 minutes at 25° C., and then 5 drops of N-methylmorpholine are added. The solution is cooled to ca. 0° C. and 1.44 ml. (0.030 mol) of ethyl chloroformate is added. The mixture is stirred for 10 minutes at 0°–5° C., and then an additional 1.44 ml. of ethyl chloroformate is added and stirring is continued for another 10 minutes. To the solution of the mixed anhydride thus obtained, is added a solution prepared from 6.65 g. (0.015 mol) of 6-(D-2-amino-2-[-4-hydroxyphenyl]-acetamido)-2,2-dimethyl-3-(5-tetrazolyl)penam trihydrate, 2.10 ml. (0.015 mol) of triethylamine and 50 ml. of hexamethylphosphoramide, at 0°–5° C. The resulting mixture is stirred for 35 minutes while it is allowed to warm slowly to 25° C. At this point the reaction mixture is diluted with 1,000 ml. of water and then filtered through a pad of celite (a diatomaceous silica product). The filtrate is added to a further 1,000 ml. of water, with the pH of the water being maintained at 2.5 during the addition by the addition of 6N hydrochloric acid. This causes a solid to precipitate. After stirring the mixture at ca 0° C. for 15 minutes, the precipitate is removed by filtration under nitrogen. The resulting solid is washed with water, followed by ether, and then dried, giving 3.7 g. of the title compound. The product is purified further by trituration with acetone and drying. The final yield is 3.6 g. (43% yield).

EXAMPLE II 6-(D-2-[-4-Hydroxy-1,5-naphthyridine-3-carboxamido]-2-[4-hydroxyphenyl]acetamido)-2,2-dimethyl-3-(5-tetrazolyl)penam Sodium Salt A suspension of 6.0 g. of 6-(D-2-[4-hydroxy-1,5-naphthyridine-3-carboxamido]-2-[4-hydroxyphenyl]acetamido)-2,2-dimethyl-3-(5-tetrazolyl)penam in 450 ml of water is stirred at 25° C.; and 1N sodium hydroxide is added slowly until a constant pH of 7.0 is obtained. The small amount of insoluble material is removed by filtration, and the filtrate is lyophilized to give the title sodium salt (6.6 g). The infrared spectrum of the product (KBr disc) shows absorption bands at 3400, 1770, 1655, 1575, 1550, 1540, 1520, 1470, 1430, 1380, 1330, 1250 and 1210 cm$^{-1}$. The nuclear magnetic resonance spectrum (in a mixture of $D_2O$ and $(CD_3)_2SO$) shows absorption bands at 9.15–8.8 (multiplet, 2H), 8.5–8.1 (multiplet, 1H), 8.1–7.7 (multiplet, 1H), 7.45 (doublet, 2H), 6.85 (doublet, 1H), 6.1–5.8 (multiplet, 1H), 5.8–5.4 (multiplet, 2H), 5.2 (singlet, 1H), 1.6 (singlet, 1H) and 1.0 (singlet, 1H), the absorption bands being expressed in parts per million downfield from internal tetramethylsilane.

EXAMPLE III 6-(D-2-[4-Hydroxy-1,5-naphthyridine-3-carboxamido]-2-[4-hydroxyphenyl]acetamido)-2,2-dimethyl-3-(5-tetrazolyl)penam Potassium Salt The procedure of Example II is repeated, except that the 1N sodium hydroxide solution used therein is replaced by 1N potassium hydroxide. This affords the potassium salt of 6-(D-2-[4-hydroxy-1,5-naphthyridine-3-carboxamido]-2-[4-hydroxyphenyl]acetamido)-2,2-dimethyl-3-(5-tetrazolyl)penam.

PREPARATION

4-Hydroxy-1,5-naphthyridine-3-carboxylic Acid

A. Diethyl 2-([3-pyridylamino]methylene)malonate

A mixture of 23.5 g. (0.25 mol.) of 3-aminopyridine and 54 g. (0.25 mol.) of diethyl 2-ethoxymethylene)-malonate is heated with stirring for 1 hour at 155° C. The mixture is cooled to 25° C., whereupon it solidifies. The solid is broken up using a pestle, giving 64.5 g. (98% yield) of diethyl 2-([3-pyridyl-amino]methylene)malonate.

B. Ethyl 4-hydroxy-1,5-naphthyridine-3-carboxylate

A mixture of 265 g. of diphenyl and 735 g. of diphenyl ether is heated to 255° C., and then the above diethyl 2-([3-pyridylamino]methylene)-malonate is added all at once. The temperature of the mixture is maintained at 255° C. until ethanol is no longer evolved. The mixture is cooled to 25° C. and the precipitate is removed by filtration. It is washed liberally with hexane and dried. This affords 40.5 g. (75% yield) of ethyl 4-hydroxy-1,5-naphthyridine-3-carboxylate.

C. 4-Hydroxy-1,5-naphthyridine-3-carboxylic acid

To a solution of 8.0 g. (0.2 mol.) of sodium hydroxide in 200 ml. of water is added 20.0 g. (0.0917 mol.) of ethyl 4-hydroxy-1,5-naphthyridine-3-carboxylate. The mixture is heated under reflux for 6 hours, and then the hot solution is treated with decolorizing charcoal and then filtered hot. The filtrate is cooled to 25° C. and acidified to pH 3 with 6N hydrochloric acid. The mixture is then cooled in an ice-bath for 15 minutes and the precipitate is removed by filtration. The solid obtained is washed with water, followed by ether, followed by acetone, and dried. This affords 11.2 g. (64% yield) of 4-hydroxy-1,5-naphthyridine-3-carboxylic acid.

What is claimed is:

1. The compound of the formula

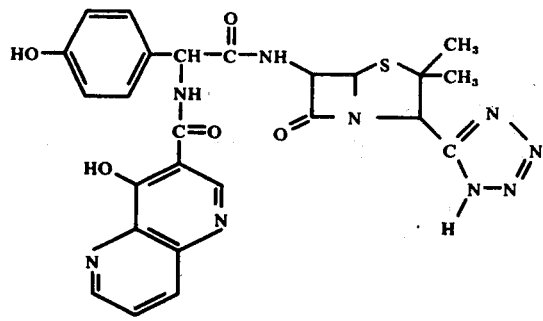

and the pharmaceutically-acceptable base salts thereof.

2. The compound of claim 1 of the formula

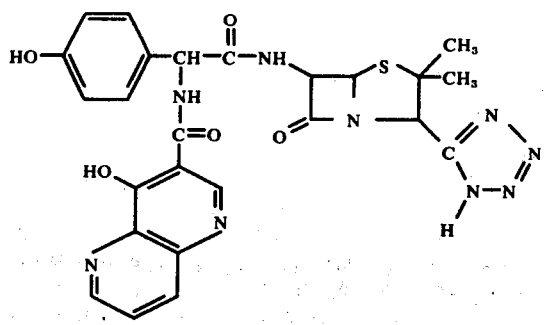

3. The pharmaceutically-acceptable salts according to claim 1, wherein the cation is sodium.

4. The pharmaceutically-acceptable salt according to claim 1, wherein the cation is potassium.

* * * * *